United States Patent [19]

Lavoisier

[11] Patent Number: 4,747,415
[45] Date of Patent: May 31, 1988

[54] METHOD AND DEVICE FOR MEASURING PENILE RIGIDITY

[76] Inventor: Pierre Lavoisier, 743 Stuart, Outremont, Quebec, Canada

[21] Appl. No.: 90,393

[22] Filed: Aug. 27, 1987

Related U.S. Application Data

[63] Continuation of Ser. No. 874,610, Jun. 16, 1986.

[51] Int. Cl.$^4$ .............................................. A61B 5/10
[52] U.S. Cl. .................................. 128/774; 128/694
[58] Field of Search ............... 128/774, 694, 672, 677, 128/686

[56] References Cited

U.S. PATENT DOCUMENTS

| | | | |
|---|---|---|---|
| 3,853,118 | 12/1974 | Schendel | 128/782 |
| 4,103,678 | 8/1978 | Karacan et al. | |
| 4,202,347 | 5/1980 | Sacks | 128/677 |
| 4,258,720 | 3/1981 | Flowers | |
| 4,314,480 | 2/1982 | Becker | |
| 4,354,503 | 10/1982 | Gidden | 128/677 |
| 4,469,108 | 9/1984 | Goldstein | |
| 4,474,187 | 10/1984 | Timm et al. | |
| 4,515,166 | 5/1985 | Timm | 128/774 X |
| 4,524,777 | 6/1985 | Kisioka et al. | 128/694 X |

OTHER PUBLICATIONS

Darling et al., Surgery, vol. 72, No. 6, Dec. 1972, pp. 873-878.
J. P. Meehan et al., High Pressure Within Corpuse Cavernosum in Man During Erection, Urology, Apr. 1983, vol. 19, No. 4.
R. Virag, Undated Advertising Brochure of the Firm Sofimec Advertising the Apparatus Known as Rigidity Meter.

Primary Examiner—Kyle L. Howell
Assistant Examiner—John C. Hanley
Attorney, Agent, or Firm—Foley & Lardner, Schwartz, Jeffery, Schwaab, Mack, Blumenthal & Evans

[57] ABSTRACT

A method and a device for measuring the penile rigidity of a patient. The device comprises a cuff including a non-elastic tissue band having one of its faces entirely covered with a plastic container filled up with a liquid. A VELCRO strap is provided for ridigity wrapping up the non elastic tissue band around the penis of the patient, with the liquid container in direct contact with the penis. A pressure transducer is mounted in direct communication with the liquid inside the plastic container for sensing the liquid pressure inside this container. An electronic device is provided for amplifying the pressure signal given by the transducer and for recording and displaying the same. In use, any erection of the penis causes an increase in penile pressure, which, in turn, comprises the liquid inside the container held in position by the cuff. Such a compression recorded by the electronic device, is, in practice, directly related to the penis rigidity of the patient.

9 Claims, 4 Drawing Sheets

METHOD AND DEVICE FOR MEASURING PENILE RIGIDITY

This application is a continuation of application Ser. No. 874,610, filed June 16, 1986.

BACKGROUND OF THE INVENTION

1. Field of the Invention

The present invention is concerned with a new method for measuring penile rigidity and with a new device for carrying out this method.

2. Brief Description of the Prior Art

Measurement of nocturnal penile tumescence hereinafter referred to as NPT, as developed by Fisher et al (see "The assessment of nocturnal REM erection in the differential diagnosis of sexual impotence.", Journal of Sex & Marital Therapy. 1975, 1(4), 277–289; and "Evaluation of nocturnal penile tumescence in the differention diagnosis of sexual impotence"; Archive of General Psychiatry, 1979, 36, 431–437) and Karacan (see "Clinical value of nocturnal erection in the prognosis and diagnosis of impotence," Medical Aspects of Human Sexuality, 1970, 4, 27–34; see also U.S. Pat. No. 4,103,678), has become the most widely used technique to establish a differential diagnosis between an organic and a psychogenic erectile dysfunction. Such a diffferential diagnosis appears to be essential for the implementation of therapeutic interventions, which can range from vascular surgery to psychoanalysis.

The standard method for measuring NPT makes use of a mercury strain gauge comprising a loop-shaped silastic tubing filled up with mercury. The tubing is positionned around the patient's penis and is connected to an electrical circuit for measuring its electrical resistance. Any change in the penile circumference causes stretching of the mercury column within the silastic tubing. Such a stretching in turn triggers a change in the mercury resistance, which can be translated into penile circumference increases.

If measurement of NPT remains an invaluable tool for diagnostic purposes, it has proved to be inefficient to measure penile rigidity, which can be defined as the state of penile firmness which is sufficient to allow vaginal penetration. Such a state of firmness can be translated into a measure of penile pressure. Since the silastic tubing used as NPT strain gauge, has an inherent elastic property, it is drastically restricted in use to the measurement of penile circumference and cannot accurately measure changes in penile pressure.

Several authors have emphasized the importance of assessing penile rigidity, in addition to NPT, in order to establish a more define differential diagnosis between organic and psychogenic erectile dysfunction. Clinical reports indicate that 17% of the patients who show normal penile tumescence on NPT recordings, actually have insufficient penile rigidity to allow vaginal penetration.

Various techniques have been developped to assess penile rigidity.

Some authors have used inferential techniques based on NPT recordings, such that 80% of maximal penile tumescence or 15 mm increase in penile circumference, correspond to sufficient penile rigidity to allow vaginal penetration. Dhabuwala et al (see "Penile calibration for nocturnal penile tumescence studies", Urology, 1983, 22, 614–616) however, have showed that the percentage of maximal tumescence required for sufficient penile rigidity varies between 53% and 92% across individuals. Such inter-subject variability makes the use of inferential techniques questionable.

Other investigators have used a waking method to directly assess penile rigidity. Some authors have asked the subjects to directly estimate the extent of penile rigidity during nocturnal erections, while others have estimated rigidity in conjunction with subject estimates. Karacan (see above) went a step further, and attempted to objectively measure penile rigidity using the buckling force technique. Once erection was observed from NPT, two constraint gauges were placed on the penile shaft and a constant weight, which does not usually triggers noticeable flexion of the penis, was applied on the glans penis. If the buckling force involves flexion of the penis, the author concludes that penile rigidity is insufficient to allow vaginal penetration. Although this technique presents advantages over subjective evaluations, it does not allow precise measurement of penile rigidity and it remains vulnerable to individual variability.

Other investigators have devised a technique consisting of surrounding the penile shaft with a continuous ring of stamps (see U.S. Pat. No. 4,474,187). Upon awakening in the next morning, the patient inspects whether the stamp ring has been broken. If so, the authors conclude that erection was sufficient to allow vaginal penetration. Although this method is an improvement over subjective evaluations, it remains vulnerable to extraneous variables such as the patient movements during the night, or the degree of humidity of the penis, which can both brake the stamp ring. Moreover, this method does not indicate the duration of the erection.

Other more objective measurements of penile rigidity have been investigated. Ek et al. (see "Nocturnal penile rigidity measured by the snap-gauge band", The Journal of Urology, 1983, 129, 964–966) have devised a snap-gauge band with three plastic films that have releasing forces of 10, 15, and 20 onces, respectively. Upon erection, the tearing of a given plastic film indicates the amount of force expended, which reflects penile rigidity. The procedure, however, does not allow continuous measurement of penile rigidity, and does not indicate the frequency and the duration of nocturnal erections.

Meehan and Golstein (see "High pressure within corpus cavernosum in man during erection. Its probable mechanism", Urology, 1983, 21, 385–387) have suggested to use a lucite cuff device consisting of two semicircular metal plates attachable to each other over an erected penis by means bolts. The plates hold a small test bladder against a lateral aspect of the penis. The bladder is connected to a pressure transducer which is itself connected to an amplifier with recorder. In use, the bladder is filled up progressively with a seryngue to compress the penis while the pressure is being measured. As the bladder starts to compress the penis, a plateau in the pressure rise can be noted, which can be taken as a measure of the intracorporal pressure. This particular method is interesting but is very uncomfortable for the patient. In addition, this method is an "active" method which requires the presence of a doctor or a nurse to carry out the testing.

The U.S. firm DACOMED of Minneapolis has also devised a "rigiscan" consisting of a loop that self-adjusts over the penis. Upon discrete intervals, the loop constricts over the penis and a mechanic force is applied, and translated into a measure of penile rigidity.

Virag et al. (see "A new device for measuring penile rigidity," Urology, 1985, 25, 80–81) have developed a device consisting of a sensor supported by a metallic arch. The sensor covers one third of the penile circumference and is attached to an elastic strip which surrounds the remaining two third of the penis. The device is connected to an electronic dynamometer which translates morphologic changes of the penis into a measure of penile rigidity.

The above methods and devices represent definite advancements in the assessment of penile rigidity. The Dacomed's device, however, involves relatively numerous and expensive computer equipment, and its validation, which uses the buckling force devised by Karacan, is to be improved. The Meehan and Golstein technique as well as the Virag et al. technique both relate penile rigidity to ICP measures, which provides adequate validation for their measuring devices. The Meehan and Goldstein device, however, is very uncomfortable for the patients and can of course not be used over an entire night of testing, while the patient is sleeping. On the other hand, The Virag et al device makes use of an elastic penile cuff, which obviously curtails accurate measurements.

SUMMARY OF THE INVENTION

The object of the present invention is to provide a non-invasive method for measuring the penile rigidity of a patient, which overcomes all of the above mentioned drawbacks.

The method and device according to the invention are intended to provide a continuous and passive measurement of penile rigidity, and the validation of the results obtained therewith is based on its relationship to the changes in intracavernous pressure (ICP).

More particularly, the present invention proposes a method for measuring the penile rigidity of a patient, comprising the steps of:

positioning a plastic container filled up with a liquid in direct contact with the penis of the patient, wrapping up a non-elastic tissue band and the plastic container around the penis of the patient to rigidly hold the plastic container against the penis of the patient;

sensing the liquid pressure inside the liquid container, and amplifying, recording and/or displaying the sensed pressure, whereby any erection of the penis causes an increase in penile pressure which, in turn, compresses the liquid inside the container held in position around the patient penis, said compression being directly related to the penile rigidity of the patient.

This method is advantageously carried out while the patient is sleeping.

The present invention also proposes a device for reducing into practise the above mentioned method, which device comprises:

(a) a cuff comprising a non-elastic tissue band having one of its face entirely covered with a plastic container filled up with a liquid;

(b) means for rigidly wrapping up the non-elastic tissue band around the penis of the patient with the liquid container in direct contact with said penis;

(c) a pressure transducer in direct communication with the liquid inside the plastic container for sensing the liquid pressure inside this container; and (d) electronic means for amplifying the pressure signal given by the transducer and for recording or displaying the same; whereby any erection of the penis causes an increase in penile pressure which, in turn, compresses the liquid inside the container held in position by the cuff, such a compression recorded by said electronic means being itself directly related to the penile rigidity of said patient.

BRIEF DESCRIPTION OF THE DRAWINGS

The invention and is advantages will be better understood upon reading the following non-restrictive description of a preferred embodiment thereof, and of tests carried out with such an embodiment, said description being given with reference to the accompanying drawings wherein.

DESCRIPTION OF A PREFERRED EMBODIMENT AND REPORT OF TESTS CARRIED OUT ONTO PATIENTS WITH THIS EMBODIMENT

Thirteen patients consulting the "Centre d'Etudes pour les Dysfonctions Sexuelles" at the "Hotel Dieu de Montreal" Hospital, voluntarily participated to this study. The patients consulted the Center for an erectile dysfunction but presented a normal NPT based on Fisher's and Karacan's criteria. Preliminary tests included the assessment of penile blood flow to ascertain that no patient suffered from venous leakage, which would have prevented the induction of an artificial erection.

The measurement procedure consisted of simultaneously measuring changes in the Intracavernosus Pressure (hereinafter referred to as ICP) and changes in penile rigidity of the patient with a device according to the invention during artificially induced erections.

Figure 1:
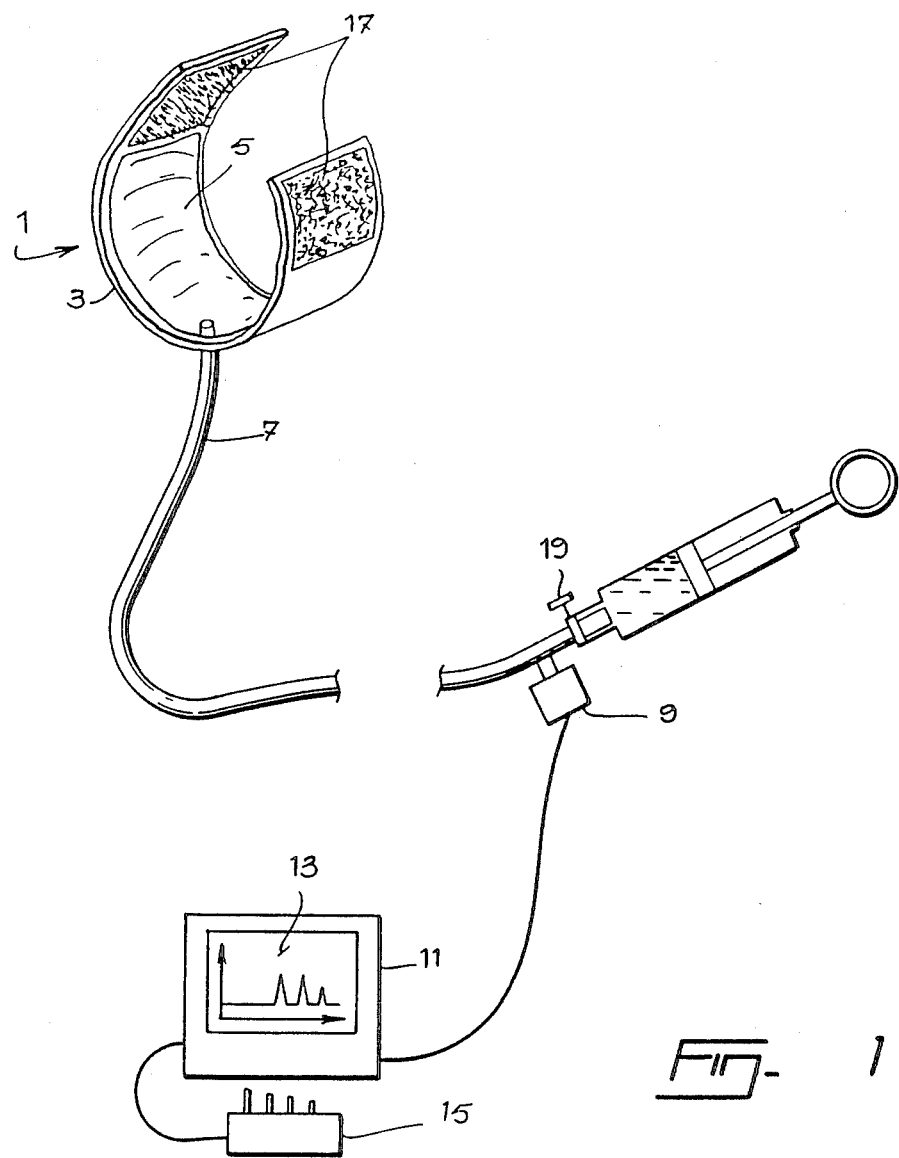
FIG. 1 is a diagrammatic representation of a device according to the invention, making use of a penile cuff (PC) for measuring the penile rigidity onto a patient.

The device according to the invention used during these tests for measuring penile rigidity, is shown in FIG. 1. This device comprises a penile cuff 1 of the type used by MEDASONIC for Doppler ultrasonography. The cuff 1 comprises a non-elastic tissue band 3 of 12 cm×2.5 cm, having one of its face entirely covered with a plastic container 5 which can be filled with a non-compressible liquid, such as water, by means of a syringe that can be subsequently removed thanks to a small tap 19. The container 5 of the penile cuff 1 is in direct communication via a tube 7, with a standard pressure transducer 9 which senses the changes in water pressure inside the plastic container 5. The signals sensed by the transducer 9 are amplified by an amplifier and recorded into the memory of a computer 11 from which they can be called back whenever desired, then treated and finally displayed on an oscilloscope 13 and/or printed on a polygraph 15 (Visicorder).

During testing, the penile cuff 1 is wrapped around the patient penis (not shown) with the plastic container 5 in direct contact against the penis. The cuff 1 is closed with a VELCRO strap 17 and can be reinforced with a tape (not shown) if necessary. When erection occurs, the increase in penile pressure compresses the water in the plastic container 5 of the penile cuff 1. Such compression triggers an increase in the water pressure which is sensed by the transducer 9 and recorded. The so recorded variation can be displayed onto the oscilloscope 13 or traced on the polygraph 15.

In order for the penile cuff 1 to accurately measure changes in pressure, the tissue band 3 must of course show no sign of elasticity.

The changes in ICP of the patients were assessed following an artificially induced erection. The procedure briefly consisted in anaesthetizing the penis of the patient with 1% xylocaine, and inserting a butterfly needle in the left corpus cavernosum. The needle was connected to a TRAVENOL blood pump which perfused physiological saline at a controlled flow. A second butterfly needle then was inserted in the right corpus cavernosum to measure changes in the intracavernosus pressure. This needle was connected to a pressure tubullure which was itself connected to a pressure transducer. The signal from the pressure transducer was amplified and recorded on a polygraph. Then, simultaneous calibration of the penile cuff 1 of the device according to the invention and of the standard and ICP device was carried out.

The calibration procedure consisted in connecting the pressure transducers of both the penile cuff 1 and the ICP to a test bladder. The amount of pressure induced from the test bladder was recorded from a mercury gauge, for changes in pressure varying between 0 mmHg and 300 mmHg, and from a water manometer, for changes in pressure varying from 300 mmHg and 1100 mmHg. As pressure was introduced from the test bladder, the amplifiers from both the penile cuff and the ICP were adjusted to get the same units of measurement on the polygraph recordings. The pressure from the test bladder was then gradually increased from 0 mmHg to 1100 mmHg and the curves from the penile cuff and the ICP recordings were compared. Both curves were found to overlap with a few exceptions where the extent of separation was within 1% error.

During the tests carried out in the hospital, each patient underwent four testing trials. The first trial consisted of inducing an artificial erection, and recording ICP changes, without use of the penile cuff 1 according to the invention. This first test was carried out to compare it with subsequent tests carried out with the penile cuff 1, to determine whether the cuff itself induced changes in ICP.

The initial trial was followed by three trails, each consisting of an artificial erection with ICP and penile cuff recordings. These three trials differed in the amount of water injected in the plastic container of the penile cuff. The volumes consisted of 5 cc, 6 cc, and 7 cc, respectively. The purpose of using different water volumes was to ensure that the penile cuff tightly surrounded the patients' penis despite individual differences in penile circumference at flaccid state.

Figure 2:
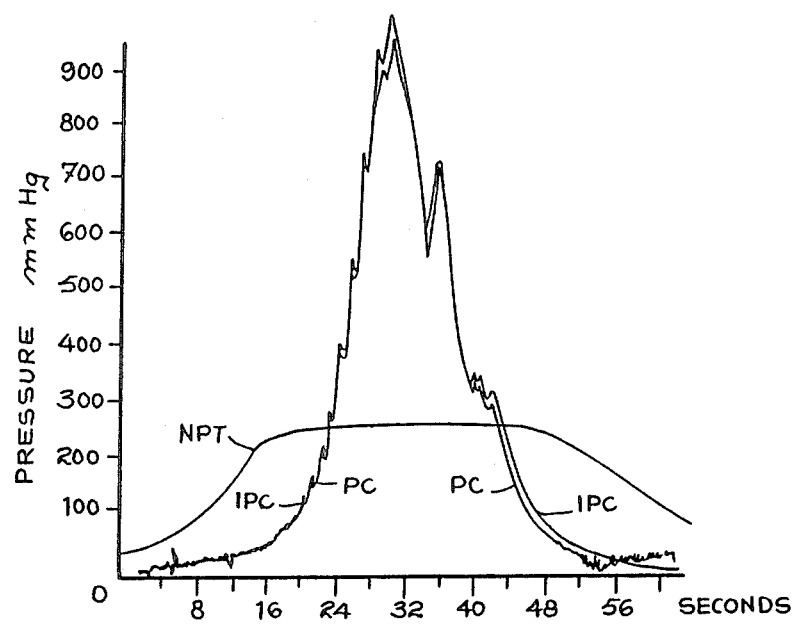
FIG. 2 are typical NPT (nocturnal penile tumescence), ICP (Intracavernosus Pressure) and PC (penile cuff) recordings made on a patient.

FIG. 2 illustrates typical sample NPT, ICP and PC (penile cuff) recordings simultaneously made on a same patient. The measurement made with the penile cuff 1 (PC) was carried out with 6 cc of water injected in the plastic container 5 of the penile cuff 1.

As can be seen from the curves, the NPT recording shows rapid increase followed by a plateau. The plateau indicates that no further increase in penile circumference can be achieved. This maximal increase occured when the ICP reached values within the 200 mmHg the Penile cuff (PC) curves undergo much drastic increase than the NPT, and peak at values above the 900 mmHg. Furthermore, both ICP and PC curves further overlap, which illustrates the perfect correspondance between both physiological measurements made on the patient. The correspondance between the measurements is demonstrated statistically by the correlation coefficient of $r = 0.999$ ($p < 0.001$) for this particular patient.

Figure 3:
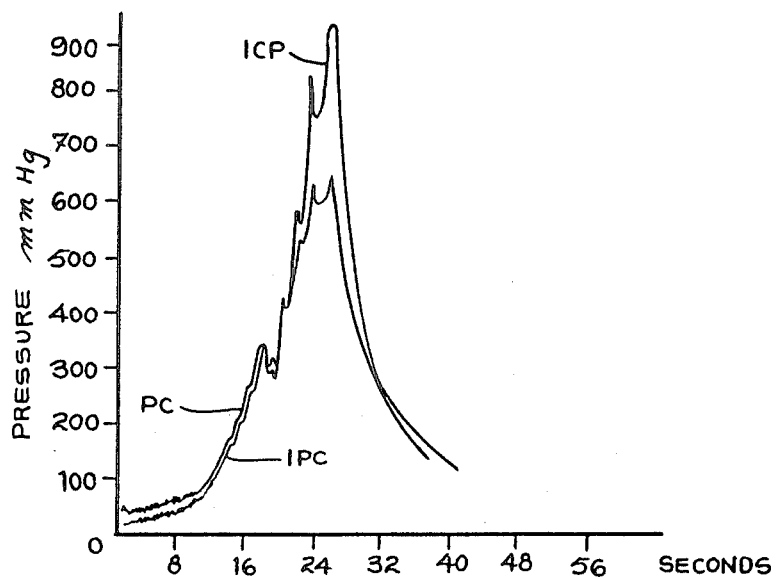
FIG. 3 are typical ICP and PC recordings made on another patient.

FIG. 3 shows recordings made on another patient with 7 cc of water injected in the penile cuff (PC). The ICP curve, again, reaches values above 900 mmHg. Although the PC recording for this patient peaks at lower values than that of the preceeding patient, both the ICP and the PC curves follow a linear function which is illustrated by the highly positive correlation coefficient of $r = 0.9993$ ($p < 0.001$) between both physiological measures.

Correlation coefficients were similarly computed for each of the tested patients, and for each volume of water injected in the penile cuff. The coefficients are illustrated on Table 1 to 3. Table 1 shows that the correlations between the ICP and the PC curves for 5 cc of injected water range from $r = 0.98$ ($p < 0.001$) to $r = 0.99$ ($p < 0.001$). The overall correlation for this water volume is $r = 0.98$ ($p < 0.001$). Table 2 shows that the correlations for the 6 cc of water range from $r = 0.97$ ($p < 0.001$) to $r = 0.99$ ($p < 0.001$). The overall correlation for this water volume is $r = 0.97$ ($p < 0.001$). Table 3 shows that the correlations for the 7 cc of water range from $r = 0.94$ ($p < 0.001$) to $r = 0.99$ ($p < 0.001$). The overall correlation for this water volume is $r = 0.96$ ($p < 0.001$). These correlation coefficients clearly demonstrate that there is a highly positive linear relationship between changes in ICP and changes in PC, thereby making the non invasive method and device according to the invention very reliable in use.

Since 5 cc and 6 cc of water injected into the penile cuff 1 of the device according to the invention showed somewhat less variability than 7 cc of water, data from both of these water volumes were combined together and used for further statistical analysis. The data from these water volumes are plotted on the scatter diagramm shown in FIG. 4.

Figure 4:
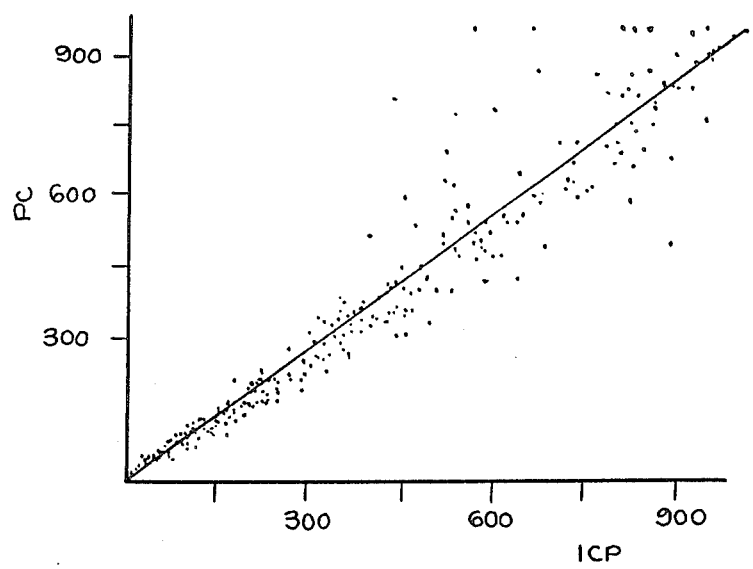
FIG. 4 is a scatter diagramm showing the existing correlation between the ICP and PC recordings made of different patients.
Figure 5:
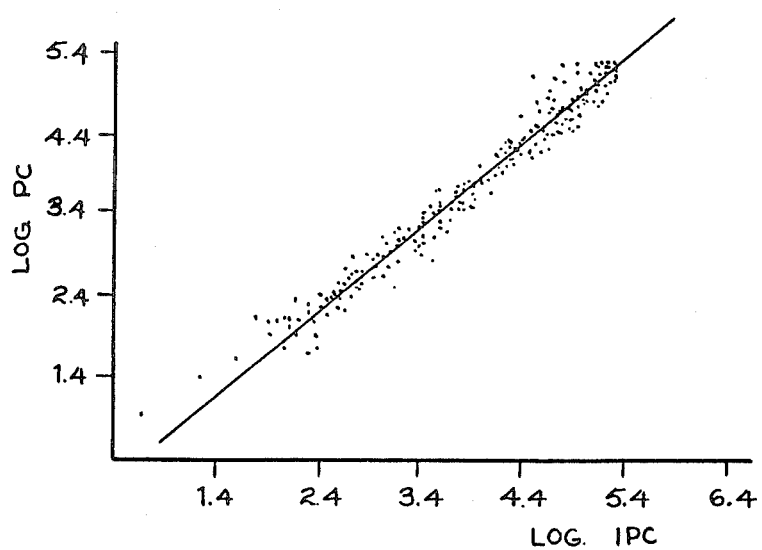
FIG. 5 is a logarithmic transformed, scatter diagramm illustrative of the correlation between the ICP and PC recordings made of different patients.
Figure 6:
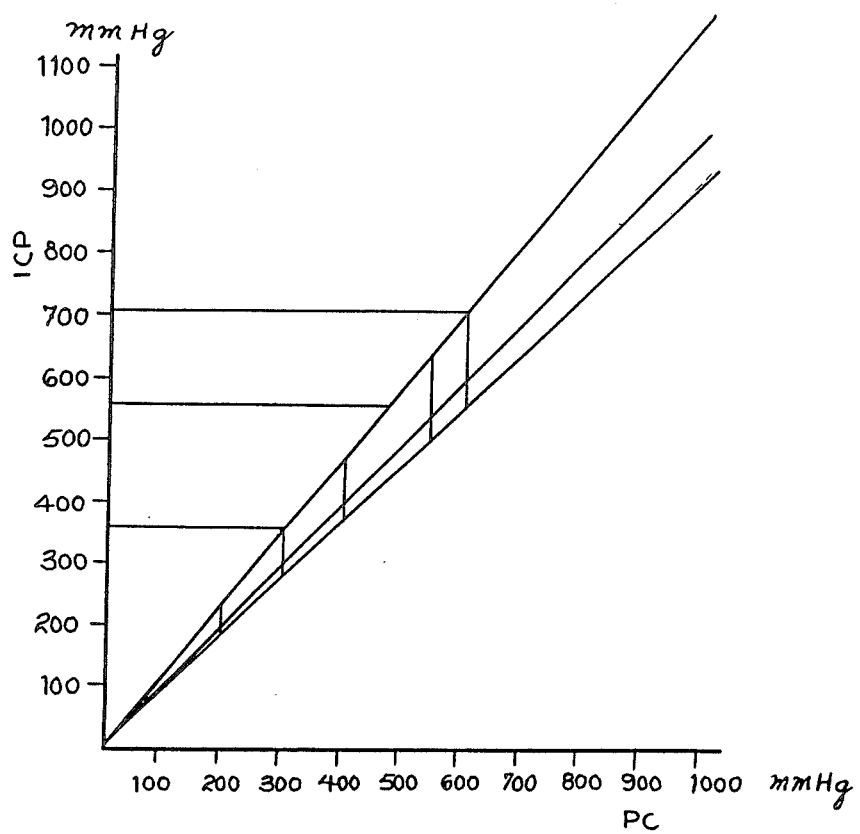
FIG. 6 is a predication curve, giving ICP values from PC values measured onto a patient.

As can be seen, the data plotted in FIG. 4 show small variability at low pressure values, but become more scattered at high pressure values. Since the scattering followed a logarithmic function, a logarithmic transformation was applied on individual date. The scatter diagram resulting from this transformation is illustrated on FIG. 5. As can be seen from the Figure, little scattering remains following data transformation, and the regression line for these data is very close to the 45 degree line with zero intercept. Such a function clearly demonstrates the existence of a highly positive linear relationship between the ICP and the PC recording which suggests good prediction of one value from the other. A regression analysis was preformed on the transformed data to predict ICP values from PC values, with a 95% confidence interval. The prediction curve, reconverted into original values, is shown on FIG. 6. This FIG. 6 shows that for PC values of 300 mmHg, ICP values can be expected to range from approximately 300 mmHg to 350 mmHg. At 600 mmHg, the ICP values can be expected to range from approximately 600 mmHg to 700 mmHg.

The results from the above study carried out onto thirteen patients suggest that NPT recordings level off within the 200 mmHg pressure range while both the ICP and the PC pressures exceed 900 mmHg. The results from the NPT recordings suggest that changes in penile circumference during erection reach a plateau from which no further increase in penile circumference can be achieved. This plateau can be explained by the mechanism underlying changes in penile circumference. When stimuli induce an erection, the corpora cavernosa engorge with blood and increase in volume. The corpora cavernosa, however, are enclosed in an inextensible membrane, the albuginea. When the distended volume of the corpora cavernosa reaches that of the albuginea, the inextensible property of the albuginea prevents any further increase in volume. This results in the levelling off of the NPT recording. When the maximum volume is reached, increase in blood flow persists within the corpora cavernosa. This increase is manifested as a pressure increase which is illustrated by the ICP recording. The above interpretation suggests that NPT measures penile tumescence without picking up on large changes in penile pressure. Since penile rigidity is mainly defined as intracavernous pressure, the results demonstrate that NPT is not an adaquate measure of penile rigidity.

On the other hand, the PC curves obtained with the device according to the invention shows a highly positive linear relationship between its recording and that of the ICP. Regression analysis further indicates that, at moderate pressure values, the ICP can be predicted from the PC values within a range of 50 mmHg. These findings demonstrate that the device according to the invention is a valid device for measuring penile rigidity. The invasive procedure involved in ICP measurement can therefore be replaced by the non-invasive method according to the invention, making use of a water-filled penile cuff 1.

TABLE 1

5 cc raw data

| Patient | Number of pairs of observations | correlation coefficient | probability level |
|---|---|---|---|
| 1 | — | — | — |
| 2 | 10 | r = 0.985 | p < 0.001 |
| 3 | 11 | r = 0.999 | p < 0.001 |
| 4 | 10 | r = 0.995 | p < 0.001 |
| 5 | — | — | — |
| 6 | 10 | r = 0.989 | p < 0.001 |
| 7 | — | — | — |
| 8 | — | — | — |
| 9 | — | — | — |
| 10 | 10 | r = 0.999 | p < 0.001 |
| 11 | — | — | — |
| 12 | 10 | r = 0.998 | p < 0.001 |
| 13 | 10 | r = 0.999 | p < 0.001 |
| 14 | 10 | r = 0.999 | p < 0.001 |
| 15 | — | — | — |
| overall | 81 | r = 0.981 | p < 0.001 |

TABLE 2

6 cc raw data

| Patient | Number of pairs of observations | correlation coefficient | probability level |
|---|---|---|---|
| 1 | 9 | r = 0.972 | p < 0.001 |
| 2 | 11 | r = 0.998 | p < 0.001 |
| 3 | 10 | r = 0.998 | p < 0.001 |
| 4 | 10 | r = 0.990 | p < 0.001 |
| 5 | — | — | — |
| 6 | — | — | — |
| 7 | 10 | r = 0.999 | p < 0.001 |
| 8 | 12 | r = 0.980 | p < 0.001 |
| 9 | 10 | r = 0.989 | p < 0.001 |
| 10 | 10 | r = 0.998 | p < 0.001 |
| 11 | 9 | r = 0.998 | p < 0.001 |
| 12 | 10 | r = 0.995 | p < 0.001 |
| 13 | 10 | r = 0.995 | p < 0.001 |
| 14 | 10 | r = 0.985 | p < 0.001 |
| 15 | — | — | — |
| Overall | 121 | r = 0.971 | p < 0.001 |

TABLE 3

7 cc raw data

| Patient | Number of pairs of observations | correlation coefficient | probability level |
|---|---|---|---|
| 1 | 10 | r = 0.993 | p < 0.001 |
| 2 | 11 | r = 0.996 | p < 0.001 |
| 3 | 10 | r = 0.993 | p < 0.001 |
| 4 | — | — | — |
| 5 | — | — | — |
| 6 | — | — | — |
| 7 | 10 | r = 0.997 | p < 0.001 |
| 8 | 9 | r = 0.995 | p < 0.001 |
| 9 | — | — | — |
| 10 | 10 | r = 0.991 | p < 0.001 |
| 11 | 10 | r = 0.948 | p < 0.001 |
| 12 | — | — | — |
| 13 | 10 | r = 0.977 | p < 0.001 |
| 14 | 10 | r = 0.995 | p < 0.001 |
| 15 | 10 | r = 0.994 | p < 0.001 |
| Overall | 100 | r = 0.962 | p < 0.001 |

The embodiments of the invention in which an exclusive property or privilege is claimed are defined as follows:

1. A method for measuring the penile rigidity of a patient comprising the steps of:
   placing a plastic container on a face of a cuff comprising a non-elastic tissue band;
   filling said plastic container with a liquid prior to use;
   wrapping said cuff around the penis of the patient while the penis is non-erected, with said filled plastic container in direct contact with the penis;
   closing said cuff to rigidly hold said filled plastic container against the penis of the patient;
   sensing the liquid pressure inside said filled plastic container, and
   amplifying and then recording and/or displaying the sensed pressure,
   whereby any erection of the penis causes an increase in penile pressure which, in turn, compresses the liquid inside the container held in position around the patient's penis, said compression causing an increase in sensed pressure and being directly related to the penile rigidity of the patient.

2. The method of claim 1, wherein the sensing is carried out when the patient is sleeping.

3. The method of claim 1 wherein the liquid is water.

4. The method of claim 1 including measuring the duration of any increase in sensed pressure.

5. The method of claim 1 including measuring the frequency and duration of any increases in sensed pressure.

6. A method of measuring penile tumescence and rigidity of a patient comprising the steps of:
   (a) filling a plastic container positioned on a face of a non-elastic cuff with a liquid prior to use;
   (b) wrapping the cuff around the penis of the patient while the penis is in a non-erected state, with the filled plastic container in direct contact with the penis;
   (c) closing the cuff to rigidly hold the filled plastic container against the penis of the patient;
   (d) sensing the liquid pressure inside the filled plastic container; and
   (e) measuring changes in sensed pressure to ascertain both tumescence and rigidity of the penis.

7. The method of claim 6 wherein the measuring step includes amplifying and then recording and/or displaying the sensed pressure.

8. The method of claim 6 including measuring the frequency of changes in sensed pressure.

9. The method of claim 6 wherein the sensing and measuring steps are performed while the patient is sleeping.

* * * * *